United States Patent [19]

Stegmann et al.

[11] Patent Number: 4,874,885

[45] Date of Patent: Oct. 17, 1989

[54] PROCESS FOR THE PREPARATION OF MERCAPTOMETHYLPHENOLS

[75] Inventors: Werner Stegmann, Liestal; Hans R. Meier; Samuel Evans, both of Marly; Roger Martin, Tentlingen; Reto Luisoli, Höstein, all of Switzerland

[73] Assignee: Ciba-Geigy Corporation, Ardsley, N.Y.

[21] Appl. No.: 133,414

[22] Filed: Dec. 15, 1987

[30] Foreign Application Priority Data

Dec. 24, 1986 [CH] Switzerland ............ 5237/86

[51] Int. Cl.$^4$ ............... C07C 149/36; C07C 149/70; C07C 149/41
[52] U.S. Cl. .......................... 560/15; 560/10; 564/154; 564/162; 568/48; 568/50; 568/51; 568/52
[58] Field of Search ............. 568/51, 46, 48, 52, 568/53, 49, 50, 51; 560/16, 15, 10; 564/154, 162

[56] References Cited

U.S. PATENT DOCUMENTS

| | | | |
|---|---|---|---|
| 2,417,118 | 3/1947 | McCleary | 568/51 |
| 3,553,270 | 1/1971 | Wollensak | 568/51 |
| 4,304,940 | 12/1981 | Wedemeyer | 568/51 |
| 4,741,846 | 5/1988 | Evans | 568/51 |

FOREIGN PATENT DOCUMENTS 165209 12/1985 European Pat. Off. .

OTHER PUBLICATIONS

Roberts, "Basic Principles of Organic Chemistry", pp. 641-652, (1964).
F. Poppelsdorf et al., J. Chem., Soc. 1954, 1124.

*Primary Examiner*—Michael L. Shippen
*Attorney, Agent, or Firm*—Luther A. R. Hall

[57] ABSTRACT

There is disclosed a process for the preparation of compounds of formula I or II

[Structure I: phenol ring with HO-, $CH_2-S-R_1$, $R_2$, $R_3$, $R_4$ substituents]

[Structure II: bis-phenol with HO-, $CH_2-S-R_1$, $R_2$, $Z_1$, $Z_2$ substituents and -OH, $CH_2-S-R_1$, $R_2$, $Z_2$ on the other ring]

from phenols by reaction with formaldehyde and mercaptans in the presence of mono-, di- or trimethylamine or mono- or diethylamine.

The symbols $R_1$ is alkyl, hydroxy or alkoxycarbonyl substituted alkyl; alkyl; aryl, cycloalkyl or aralkyl, $R_2$ is hydrogen, alkyl, alkenyl or halogen, $R_3$ and $R_4$ are independently alkyl, allyl, cycloalkyl, phenyl, benzyl, halogen or $-CH_2-S-R_1$, $Z_1$ is $-S-$ or alkylene, and $Z_2$ is hydrogen, alkyl or $-CH_2-S-R_1$.

The mercaptomethylphenols are valuable antioxidants for plastics, elastomers, mineral oils and synthetic lubricants.

10 Claims, No Drawings

PROCESS FOR THE PREPARATION OF MERCAPTOMETHYLPHENOLS

The present invention relates to a process for the preparation of mercaptomethylphenols from phenols by reaction with formaldehyde and mercaptans.

It is known to prepare arylthiomethylanphthols or alkylthiomethylnaphthols by reaction of e.g. β-naphthol with formaldehyde and arylor alkylmercaptans in the presence of triethylamine (q.v. F. Poppelsdorf et al., J. Chem. Soc. 1954, 1124 et seq.). However, reaction times of about six days are necessary to obtain satisfactory yields.

The preparation of 2,4-mercaptomethylphenols e.g. from phenols by reaction with formaldehyde and mercaptans in the presence of dialkylamines or trialkylamines is disclosed in European patent application EP-A-O 165 209. Specifically, however, only dibutylamine is used.

As mercaptomethylphenols are valuable antioxidants, there is still a need for an improved process for obtaining them. It has now been found that mercaptomethylphenols can be obtained in high yield and purity in conveniently short reaction times by carrying out the reaction in the presence of a methylamine or ethylamine.

Accordingly, the present invention relates to a process for the preparation of compounds of formula I or II

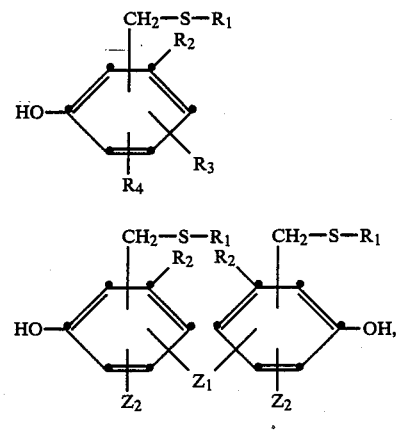

wherein $R_1$ is $C_1$-$C_{20}$alkyl which is unsubstituted or substituted by 1 or 2 hydroxyl groups or interrupted by —O—, or is $C_1$-$C_4$alkylene-COOR$_5$, $C_1$-$C_4$alkylene-CO—NR$_5$R$_6$, $C_5$-$C_{12}$cycloalkyl, phenyl, 1-naphthyl, 2-naphthyl, $C_1$-$C_4$alkylphenyl or phenyl-$C_1$-$C_4$alkyl, $R_2$ is hydrogen, $C_1$-$C_{20}$alkyl, $C_2$-$C_{18}$alkenyl or halogen, $R_3$ -C $_2$C of and $_0$alkyl, allyl, $C_5$-$C_{12}$cycloalkyl, phenyl, phenyl-$C_1$-$C_4$alkyl, halogen or —CH$_2$—S—R$_1$, with the proviso that at least one of $R_3$ and $R_4$ is —CH$_2$—S—R$_1$, $R_5$ is $C_1$-$C_{20}$alkyl, allyl, $C_5$-$C_{12}$cycloalkyl, phenyl or benzyl, $R_6$ is hydrogen, $C_1$-$C_{20}$alkyl or $C_2$-$C_{18}$alkenyl, $Z_1$ is —S— or —C($Z_3$)($Z_4$)—, $Z_2$ is hydrogen, $C_1$-$C_{20}$alkyl or -CH$_2$-S-R$_1$, $Z_3$ is hydrogen or methyl and $Z_4$ is hydrogen or $C_1$-$C_8$alkyl, with the proviso that the phenols of formula I or II in m-position do not contain the functional group —CH$_2$—S—R$_1$, by reaction of a phenol of formula III or IV

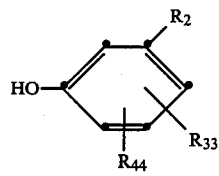

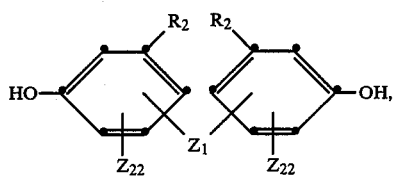

wherein $R_2$ and $Z_1$ are as previously defined, $R_{33}$ and $R_{44}$ are each independently of the other hydrogen, $C_1$-$C_{20}$-alkyl, allyl, $C_5$-$C_{12}$cycloalkyl, phenyl, phenyl-$C_1$-$C_4$alkyl or halogen, with the proviso that at least one of $R_{33}$ and $R_{44}$ is hydrogen, and $Z_{22}$ is hydrogen or $C_1$-$C_{20}$alkyl, with formaldehyde or a compound that liberates formaldehyde under the reaction conditions and with at least one mercaptan $R_1$—SH, in the presence of a base, said base being mono-, di- or trimethylamine or mono- or diethylamine.

Preferred mercaptomethylphenols obtained by the process of this invention are those of formula I, wherein $R_1$ is $C_8$-$C_{12}$alkyl, —CH$_2$—COO-alkyl containing 1 to 18 carbon atoms in the alkyl moiety, —CH$_2$CH$_2$—OH, phenyl or benzyl, and, in particular, those wherein $R_1$ is $C_8$-$C_{12}$alkyl or —CH$_2$—COO—CH$_2$—C(C$_2$H$_5$)—(CH$_2$)$_3$—CH$_3$.

Particularly preferred mercaptomethylphenols obtained by the process of this invention are those of formula

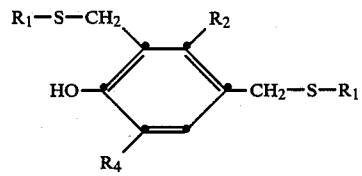

wherein $R_1$, $R_2$ and $R_4$ are as previously defined and, most particularly, those wherein $R_2$ is hydrogen or methyl and $R_4$ is methyl, tert-butyl or cyclohexyl.

Interesting mercaptomethylphenols obtained by the process of the invention are also those of formula

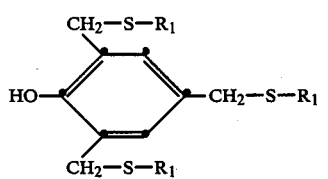

wherein $R_1$ is as previously defined.

$R_1$, $R_2$, $R_3$, $R_4$, $R_5$, $R_6$, $R_{33}$, $R_{44}$, $Z_{22}$ as $C_1$-$C_{20}$alkyl may be methyl, ethyl, n-propyl, isopropyl, n-butyl, sec-butyl, t-butyl, n-pentyl, isopentyl, n-hexyl, 1,1-dimethylbutyl, n-heptyl, n-octyl, 2-ethylhexyl, n-nonyl, n- decyl, 1,1,3,3-tetramethylbutyl, 1,1,3,3-tetramethylhexyl, n-undecyl, n-dodecyl, 1,1,3,3,5,5-hexamethylhexyl, 2,2,4,6,6-pentamethylhept-4-yl, n-tetradecyl, n-hexadecyl, n-octadecyl or n-eicosyl.

$Z_4$ as $C_1-C_8$alkyl may be methyl, ethyl, n-propyl, isopropyl, n-butyl, sec-butyl, n-pentyl, isopentyl, n-hexyl, 1,1-dimethylbutyl, n-heptyl or n-octyl, preferably $C_1-C_4$alkyl and, most preferably, methyl.

$R_2$, $R_3$, $R_4$, $R_{33}$, $R_{44}$, $Z_2$ and $Z_{22}$ as alkyl are preferably $C_1-C_4$alkyl, for example methyl, ethyl, n-propyl, isopropyl, n-butyl or tertbutyl. Most preferably, R3 and R4 are methyl or tert-butyl. $R_1$ is preferably $C_2-C_{18}$alkyl and, most preferably, $C_8-C_{12}$alkyl, for example n-octyl, 1,1,3,3-tetramethylbutyl, n-dodecyl or tert-dodecyl [a mixture of 1,1,3,3,5,5-hexamethylhexyl and 1,1,4,4,6,6-pentamethylhept-4-yl].

$R_1$ as $C_1C_{20}$alkyl substituted by 1 or 2 hydroxyl groups may be hydroxymethyl, 2-hydroxyethyl, 2-hydroxypropyl, 2-hydroxybutyl, 2-hydroxyhexyl, 2-hydroxyoctyl, 2-hydroxydecyl, 2-hydroxydodecyl, 2-hydroxytetradecyl, 2-hydroxyhexadecyl, 2-hydroxyoctadecyl, 2-hydroxyeicosyl or 2,3-dihydroxypropyl. The preferred meaning of $R_1$ is $C_1-C_4$hydroxyalkyl, for example 2-hydroxypropyl or 2,3-dihydroxypropyl and, most preferably, 2-hydroxyethyl.

$R_1$ as alkyl interrupted by —O— may be interrupted by one or more oxygen atoms, for example by 1 to 6 and, preferably, 1 or 2, oxygen atoms, and is for example 3-oxapropyl, 3-oxabutyl, 3-oxapentyl, 3,6-dioxaheptyl, 3.6,9-trioxadecyl or 3,6,9,12,15,18-hexaoxanonadecyl.

$R_2$ and $R_6$ as $C_2C_8$alkenyl may be vinyl, allyl, but-e-enyl, pent-4-enyl, hex-5-enyl, oct-7-enyl, dec-9-enyl, dodec-11-enyl or octadec-17-enyl. Vinyl or allyl is preferred.

$R_1$, $R_3$, $R_4$, $R_5$, $R_{33}$ and $R_{44}$ as $C_5-C_{12}$cycloalkyl may be cyclopentyl, cyclohexyl, cycloheptyl, cyclooctyl, cyclononyl, cyclodedyl, cycloundecyl or cyclododecyl. The preferred meaning is $C_5-C_7$cycloalkyl, with cyclohexyl being especially preferred.

$R_1$, $R_3$, $R_4$, $R_{33}$ and $R_{44}$ as phenyl-$C_1-C_4$alkyl may be benzyl, phenylethyl, α-methylbenzyl or α,α-dimethylbenzyl. Benzyl is preferred. $R_1$ as $C_1-C_4$alkylphenyl may contain 1 to 3, preferably 1 or 2, alkyl groups and is for example o-, m- or p-tolyl, 2,4-, 2,6-, 3,5- or 3,6-dimethylphenyl, ethylphenyl, propylphenyl, isopropylphenyl, tert-butylphenyl or di-tert-butylphenyl. Tolyl is preferred.

$R_2$, $R_3$, $R_4$, $R_{33}$ and $R_{44}$ as halogen may be chlorine or bromine preferably chlorine.

In the process of this invention, the phenol, formaldehyde and mercaptan reactants can be used in stoichiometric proporations. But it may on occasion be advantageous to use an excess of formaldehyde and/or mercaptan. Mixtures of phenols and/or mercaptans can also be reacted.

The process of the invention is carried out in the presence of mono-, di- or trimethylamine or mono- or diethylamine as base. It is preferred to use mono- or dimethylamine and, most preferably, dimethylamine.

The base may be for example in the form of a 10–35 % solution in ethanol, methanol or another lower alcohol or in pure form. Dimethylamine can also be used in gaseous form.

In the process of this invention, the base can be used for example in an amount of 1–50 mol %, preferably of 2–30 mol % and, most preferably, 5–20 mol %, based on the mercaptan.

The process of the invention can be carried out in the presence of a solvent.

Examples of suitable solvents are alcohols of 1 to 6 carbon atoms, for example methanol, ethanol, propanol, butanol, pentanol or hexanol. However, it is also possible to use diols, polyols and ethers thereof, for example glycol, glycerol and polyethylene glycol. The reacton can be carried out in a polar aprotic solvent such as dimethylformamide or dimethylsulfoxide, or a high-boiling aromatic or aliphatic hydrocarbon or chlorinated hydrocarbon such as toluene, ligroin or chlorobenzene may be used. The preferred solvent is dimetnylformamide, which is diluted with one of the above mentioned lower alcohols or chlorinated hydrocarbons.

It is preferred, however, to carry out the process of the invention in the absence of a solvent.

The process of this invention can conveniently be carried out in the temperature range from 80° to 160° C., preferably from 90° to 150° C. and, most preferably, from 90° to 130° C., and at normal pressure or under pressure (e.g. from 0.01 to 5 bar). In the absence of a solvent the reaction is preferably carried out under overpressure.

Depending on the specific phenol and mercaptan employed, the reaction times may vary and are for exmaple from 1 to 24 hours and, preferably, from 1 to 6 hours. The reaction mixture is conveniently heated in a nitrogen atmosphere under reflux.

After cooling to room temperature, the reaction mixture is worked up by conventional separating and purifying methods.

It is, however, a further advantage of the process of this invention that the final products are obtained in a purity that permits their direct further use.

Most of the mercaptomethyl compounds prepared by the process of the invention are known compounds. The starting phenols and mercaptans are also known and some are commercially available or can be prepared by known methods.

Formaldehyde or a compound that liberates formaldehyde under the reaction conditions, for example paraformaldehyde or hexamethylenetetramine, is used for the reaction. It is preferred to use formaldehyde, but paraformaldehyde is particularly preferred.

The compounds of formulae I and II prepared by the process of this invention can be used as stabilisers for protecting organic material from damage by the action of oxygen, heat, light or high-energy radiation. The preferred utility of these compounds is as antioxidants in organic polymers and in elastomers, or in mineral oils or synthetic lubricants as described e.g. in EP-A-O 165 209.

The stabilisers are normaly added to the plasticsor lubricants in a concentration of 0.01 to 10 % by weight, based on the material to be stabilised. It is preferred to incorporate 0.05 to 5.0 % by weight, most preferably 0.1 to 2.0 % by weight, based on the material to₁be stabilised, into said material.

Incorporation of the compounds of formulae I and II can be effected, for example, by blending them with the material to be stabilised together with further optional additives by methods conventionally employed in the art, before or during the manufacture of articles shaped from said polymer, or also by applying the dissolved or dispersed compound to the polymer, with or without subsequent evaporation of the solvent. The compounds of this invention may also be added to the materials to be stabilised in the form of a masterbatch which contains said compounds, for example, in a concentration of 2.5 to 25 % by weight.

In the case of crosslinkable polyethylene, the compounds are added prior to crosslinking.

In practice, he mercaptomethyl phenols of formulae I and II are added together with other stabilisers.

Lubricant formulations may also contain further additives which are added to improve certain use properties, for example further antioxidants, metal deactivators, rust inhibitors, viscosity index improvers, pour-point depressors, dispersants/surfactants and antiwear additives.

The invention is further illustrated by the following Examples. The purity of the compounds is determined by high pressure liquid chromatography. An absolute yield, which is indicated in brackets after the purity, is computed from the crude yields and purity.

EXAMPLE 1

Preparation of 2,4-bis(n-octylthiomethyl)-6-methylphenol

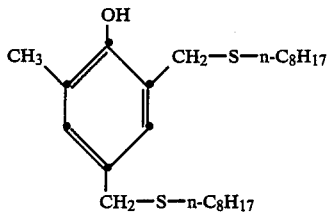

A mixture of 16.22 g (0.15 mole) of o-cresol, 43.88 g (0.3 mole) of n-octanethiol, 18.02 g (0.6 mole) of paraformaldehyde, 4.1 g of a 33 % solution of dimethylamine in ethanol (corresponding to c. 0.03 mole of dimethylamine) and 22.5 ml (21.35 g) of N,N-dimethylformamide is heated, under nitrogen, in a sulfonating flask equipped with reflux cooler and mechanical stirrer. The temperature of the reaction mixture is 115° C. The volatile constituents are then removed at a bath temperature of 90°–95° C. and under reduced pressure. The residue is subsequently dried at 100°–120° C. and 1.33 mbar, affording 61.8 g (96.9 % of theory) of 2,4-bis(n-octylthiomethyl)-6-methylphenol as a yellow liquid in a purity of 94.6 % (absolute yield: 91.7 %).

Analysis:
Theory: 70.70 % C, Found: 70.71 % C, 10.44 % H, 10.41 % H, 15.10 % S, 15.09 % S.

The subsequent Examples 2 and 3 describe process variants for the preparation of 2,4-bis(n-octylthiomethyl)-6-methylphenol in the presence of a solvent, while Examples 3 and 4 describe the solventfree preparation.

EXAMPLE 2

A mixture of 108.14 g (1 mole) of o-cresol, 292.56 g (2 moles) of n-octanethiol, 120.12 g (4 moles) of paraformaldehyde, 27.33 g of a 33% solution of dimethylamine in ethanol (corresponding to c. 0.2 mole of dimethylamine) and 50 ml (47.4 g) of N,N-dimethylformamide is heated under reflux for 2 hours as described in Example 1 (temperature of the reaction mixture: 155° C.).

After working up as described in Example 1, the product is further purified as follows: the crude product is taen up in 800 ml of hexane and the solution is washed with 4 x 200 ml of water in a separating funnel. The hexane phase is then separated and dried. The solvent is removed by distillation to give 409.5 g (96.4 % of theory) of a yellowish liquid which is identical with the compound obtained in Example 1 (confirmation by 1H-NMR spectroscopy and thin-layer chromatography) and has a purity of 97.9 % (absolute yield: 94.4 %).

EXAMPLE 3

The procedure of Example 1 is repeated using the following mixture: 16.22 g (0.15 mole) of o-cresol, 43.88 g (0.3 mole) of n-octanethiol, 18.02 g (0.6 mole) of paraformaldehyde, 22.5 ml (21.35 g) of N,N-dimethylformamide and 1.14 g (0.031 mole) of dimethylamine. The dimethylamine is passed in gaseous form into the suspension of the above components (temperature of the suspension: 20°–30° C.). Yield: 55.6g (87.2 % of theory) of 2,4-bis(n-octylthiomethyl)-6-methylphenol as a yellow liquid in 98.3 % purity (absolute yield: 87.7%).

EXAMPLE 4

An apparatus consisting of a 1 litre reaction vessel (approved for up to 2 bar overpressure) equipped with impeller, internal thermometer, distillation head with cooler and receiver with vacuum connection, nitrogen inlet and gas feed pipe, is charged at room temperature, in succession, with 194.6 g (1.80 mole) of o-cresol, 113.5 g (3.78 mole) of 100% paraformaldehyde and 526.7 g (3.60 moles) of 1-octanethiol. The suspension is blanketed with nitrogen and thereafter evacuated to c. 20 mbar with efficient stiring at room temperature (25° C.). then 9.7 g (0.216 mole) of dimethylamine in gaseous form is passed into the suspension through a gas feed pipe over 10 minutes, whereupon a marked exothermic reaction is observed, the temperature of the reaction mixture rising by c. 10%C, whereas the vacuum in the apparatus falls to c. 100 mbar.

The suspension is heated to 120° C. and stirred for 6 hours at this temperature, the pressure rising from 100 mbar to c. 2.2 bar (corresponding to an overpressure of 1.2 bar). The suspension simultaneously turns into a clear yellowish brown melt which becomes very turbid towards the end of the reaction on account of the water that forms.

The reaction mixture is cooled to 50° C. Distillation of a mixture of dimethylamine, water and some excess paraformaldehyde is effected at this temperature by applying a vacuum of 20 mbar and is complete at 100° C./20 mbar.

The clear melt is then freed from excess octanethiol by steam distillation (temperature c. 135° C.) and subsequent drying at 150° C./20 mbar, affording 690 G (90 % of theory) of 2,4-bis(n-octylthiomethyl)-6-methylphenol in 89.6 % purity (absolute yield: 80.6 %).

EXAMPLE 5

An apparatus consisting of a 350 ml sulfonating flask equipped with propeller stirrer, gas feed pipe, internal thermometer, nitrogen inlet and brine-cooled reflux cooler is charged with 32.4 g (0.30 mole) of o-cresol, 87.8 g (0.60 mole) of 1-octanethiol and 18.9 g (0.63 mole) of paraformaldehyde at room temperature. Then 4.06 g (0.09 mole) of dimethylamine are passed in gaseous form into the suspension over 10 minutes with efficient stirring, whereupon the temperature rises by c. 20° C. Under light blanketing with nitrogen, the suspension is heated to 112°–114° C., whereupon the suspension initially turns into a clear melt and reflux commences. Stirring is continued for 4 hours under reflux. The melt initially becomes turbid and then later two-phase (presence of water) and the temperature falls to 102°–104° C.

Working up is effected as described in Example 4. Yield: 120.8 g (84.8 % of theory) of 2,4-bis(n-octylthiomethyl)-6-methylphenol in 89.9 % purity (absolute yield: 76.2%).

EXAMPLE 6

Preparation of 2,4,6-tris[3'-(2''-ethylhexyloxycarbonyl)-2'-thiapropyl]-phenol

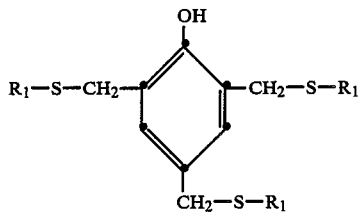

wherein

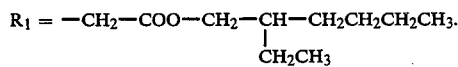

In a sulfonating flask equipped with reflux cooler and stirrer, a mixture of 18.82 g (0.2 mole) of phenol, 122.60 g (0.6 mole) of 2-ethylhexyl thioglycolate, 36.0 g (1.2 moles) of paraformaldehyde, 5.46 g of a 33 % solution of dimethylamine in ethanol (corresponding to c. 0.04 mole of dimethylamine) and 2.0 ml (1.9 g) of N,N-dimethylformamide is heated for 6 hours under nitrogen to 90° C. Then 200 ml of toluene and 100 ml of water are added and the batch is stirred briefly. The organic phase is separated in a separating funnel and evaporated to dryness. The residue is dried for 2 hours at 70° C./0.133 mbar, to give 142.7 g (96 % of theory) of 2,4,6-tris[3'-(2''-ethylhexyloxycarbonyl)-2'-thiapropyl]phenol as a clear colourless oil in 80.8 % purity (absolute yield: 77.6 %).

Analysis:
Theory: 63.03 % C, Found: 62.59 % C, 8.95 % H, 8.98 % H, 12.94 % S, 12.38 % S.

EXAMPLE 7

The procedure of Example 6 is repeated using 1.80 g (0.04 mole) of dimethylamine gas. The gas is passed into the suspension at 20°–30° C. (temperature of the suspension).

Yield: 141.2 g (95 % of theory) of a clear colourless oil which is identical with the compound obtained in Example 6 (confirmation by $^1$H-NMR spectroscopy and thin-layer chromatography) and has a purity of 82.5 % (absolute yield: 78.4 %).

EXAMPLE 8

Preparation of 2,6-bis(n-octylthiomethyl)-4-tert-butylphenol

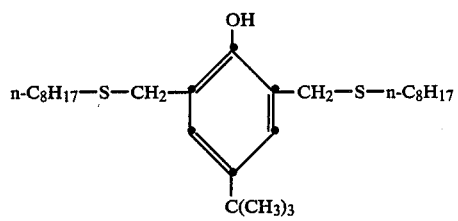

The procedure of Example 1 is repeated using the following mixture: 22.53 g (0.15 mole( of 4-tert-butylphenol, 18.02 g (0.6 mole) of paraformaldehyde, 43.88 g (0.3 mle) of n-octanethiol, 4.1 g of a 33 % solution of dimethylamine in ethanol (corresponding to c. 0.03 mole) of dimethylamine) and 22.5 ml (21.4g) of N,N-dimethylformamide. The reaction time is 3 hours.

The crude product is taken up in 150 ml of ethyl acetate and the solution is washed with 100 ml of water. The organic phase is evaporated to dryness to give 51 g (97 % of theory) of 2,6-bis(n-octylthiomethyl)-4-tert-butylphenol as a colourless oil in 93.3 % purity (absolute yield: 90.5 %).

Analysis:
Theory: 72.04 % C, Found: 71.91 % C, 10.80 % H, 10.83 % H, 13.74 % S, 13.55% S.

EXAMPLE 9

Solvent-free preparation of 2,6-bis(n-octylthiomethyl)-4-tert-butylphenol

The procedure of Example 4 is repeated using the following mixture: 240.3 g (1.6 mole) of 4-tert-butylphenol, 468.2 g (3.2 moles) of paraformaldehyde and 100.9 g (3.32 moles) of n-octanethiol. Then 8.7 g (0.19 mole) of gaseous dimethylamine are passed into the suspension. The reaction time is 3 hours. Yield: 670 g (90 % of theory) of 2,6-bis(n-octylthiomethyl)-4-tert-butylphenol in 94.1 % purity (absolute yield: 84.7 %).

EXAMPLE 10

Preparation of 2,2-bis[4,4'-dihydroxy-3,3',5,5'-tetrakis(n-octylthiomethyl)phenyl]propane

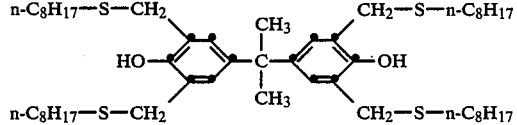

The procedure of Example 8 is repeated using the following mixture: 23.3 g (0.10 mole) of bisphenol A, 20.4 g (0.68 mole) of paraformaldehyde, 60.33 g (0.41 mole) of n-octanethiol, 7.5 g of a 33% solution of dimethylamine in ethanol (corresponding to c. 0.056 mole of dimethylamine) and 40 ml (38 g) of N,N-dimethylformamide. The reaction time is 6 hours. Yield: 86.4 g (99 % of theory) of the product as a slightly yellowish oil in 94.6 % purity (absolute yield: 93.7 %).

Analysis:
Theory: 71.10 % C, Found: 70.87 % C, 10.30 % H, 10.51 % H 14.89 % S, 14.87 % S.

EXAMPLE 11

Preparation of 2,4-bis(n-octylthiomethyl)-6-methylphenol

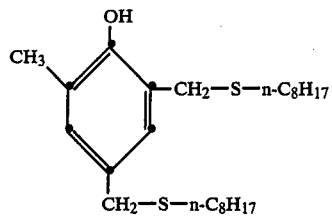

The procedure of Example 1 is repeated using 0.93 g (0.03 mole) of methylamine as base instead of 0.03 mole of dimethylamine. Yield: 60.38 g (98.5 % of theory) of the product as a yellowish liquid in 78.3 % purity (absolute yield: 77.1 %).

What is claimed is:

1. A process for the preparation of a compound of formula I or II

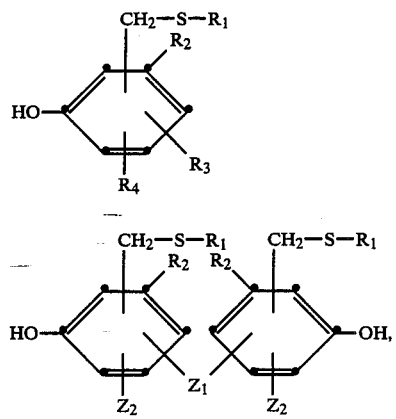

wherein $R_1$ is $C_1$-$C_{20}$alkyl which is unsubstituted or substituted by 1 or 2 hydroxyl groups or interrupted by —O—, or is $C_1$-$C_4$alkylene-COOR$_5$, $C_1$-$C_4$alkylene-CONR$_5$R$_6$, $C_5$-$C_{12}$cycloalkyl, phenyl, 1-naphthyl, 2-naphthyl, $C_1$-$C_4$alkylphenyl or phenyl-$C_1$-$C_4$alkyl, $R_2$ is hydrogen, $C_1$-$C_{20}$alkyl, $C_2$-$C_{18}$alkenyl or halogen, $R_3$ and $R_4$ are each independently of the other $C_1$-$C_{20}$alkyl, allyl, $C_5$-$C_{12}$cycloalkyl, phenyl, phenyl-$C_1$-$C_4$alkyl, halogen or —CH$_2$—S—R$_1$, with the proviso that at least one of $R_3$ and $R_4$ is —CH$_2$—S—R$_1$, $R_5$ is $C_1$-$C_{20}$alkyl, allyl, $C_5$-$C_{12}$cycloalkyl, phenyl or benzyl, $R_6$ is hydrogen, $C_1$-$C_{20}$alkyl or $C_2$-$C_{18}$alkenyl, $Z_1$ is —S— or —C(Z$_3$)(Z$_4$)—, $Z_2$ is hydrogen, $C_1$-$C_{20}$alkyl or -CH$_2$-S-R$_1$, $Z_3$ is hydrogen or methyl and $Z_4$ is hydrogen or $C_1$-$C_8$alkyl, with the proviso that the phenols of formla I or II in m-position do not contain the functional group —CH$_2$—S—R$_1$, by reaction of a phenol of formula III or IV

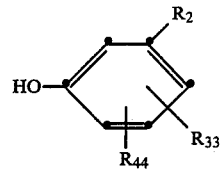

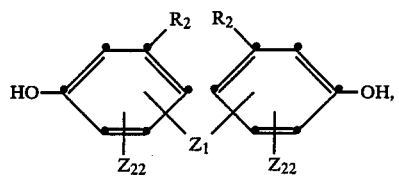

wherein $R_2$ and $Z_1$ are as previously defined, $R_{33}$ and $R_{44}$ are each independently of the other hydrogen, $C_1$-$C_{20}$-alkyl, allyl, $C_5$-$C_{12}$cycloalkyl, phenyl, phenyl-$C_1$-$C_4$alkyl or halogen, with the proviso that at least one of $R_{33}$ and $R_{44}$ is hydrogen, and $Z_{22}$ is hydrogen or $C_1$-$C_{20}$alkyl, with formaldehyde or a compound that liberates formaldehyde under the reaction conditions and with at least one mercaptan $R_1$—SH, in the presence of a base, said base being mono- or dimethylamine or mono- or diethylamine.

2. A proces according to claim 1, wherein the base is dimethylamine.

3. A process according to claim 1, wherein 1 to 50 mol % of base is used, based on the mercaptan.

4. A process according to claim 1, wherein the reaction is carried out in the absence of a solvent.

5. A process according to claim 1 for the preparation of a compound of formula

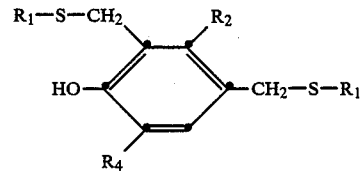

wherein $R_1$, $R_2$ and $R_4$ are as defined in claim 1.

6. A process according to claim 5, wherein $R_2$ is hydrogen or methyl and $R_4$ is methyl, tert-butyl or cyclohexyl.

7. A process according to claim 1 for the preparation of a compound of formula

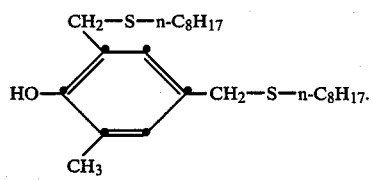

8. A process for the preparation of a compound of formula I according to claim 1, wherein $R_1$ is $C_8$-$C_{12}$alkyl, —CH$_2$—COO-alkyl containing 1 to 18 carbon atoms in the alkyl moiety, —CH$_2$—CH$_2$—OH, phenyl or benzyl.

9. A process according to claim 8, wherein $R_1$ is $C_8$-$C_{12}$alkyl.

10. A process according to claim 8, wherein $R_1$ is —CH$_2$—COO—CH$_2$—C—(C$_2$H$_5$)—(CH$_2$)$_3$—CH$_3$.

* * * * *